United States Patent [19]

Hickman et al.

[11] 4,108,167

[45] Aug. 22, 1978

[54] DENTAL SYRINGE

[75] Inventors: Clarence J. Hickman; Donald W. Ruehmann; Christopher W. Elkins, all of Ft. Collins, Colo.

[73] Assignee: Teledyne Industries, Inc., Ft. Collins, Colo.

[21] Appl. No.: 764,280

[22] Filed: Jan. 31, 1977

[51] Int. Cl.² .................................... A61H 9/00
[52] U.S. Cl. .................... 128/66; 128/62 A; 92/187
[58] Field of Search ............... 128/66, 62 A, 230, 234; 92/187

[56] References Cited

U.S. PATENT DOCUMENTS

| 3,802,323 | 4/1974 | Suechting | 92/187 |
|---|---|---|---|
| 3,811,432 | 5/1974 | Moret | 128/66 |
| 3,820,532 | 6/1974 | Eberhardt et al. | 128/66 |
| 3,874,506 | 4/1975 | Hill et al. | 128/66 |

Primary Examiner—Lawrence W. Trapp
Attorney, Agent, or Firm—Hugh H. Drake

[57] ABSTRACT

A hygienic device has a pump for propelling liquid in a flow of pulses, a motor for driving the pump, a switch for supplying power to the motor and means for delivering the propelled liquid to a point of use. A control enables adjustment of the pressure of the delivered liquid. The switch is formed as part of the motor winding assembly and therewith is effectively encapsulated. The pump includes a piston in one end of which is a recess defining a resilient spherical seat and which cooperates with a spherical bearing formed on one end of a piston rod. The control has a valved bypass arrangement wherein various stops and abutments cooperate to permit accurate determination of high and low pressure adjustment during assembly. A rotor within the motor has a cylindrical bore with longitudinal lugs that interfit with ribs on a bearing member that is pressed into the bore. Other features, such as a tilt-out nozzle storage shelf, are included.

12 Claims, 31 Drawing Figures

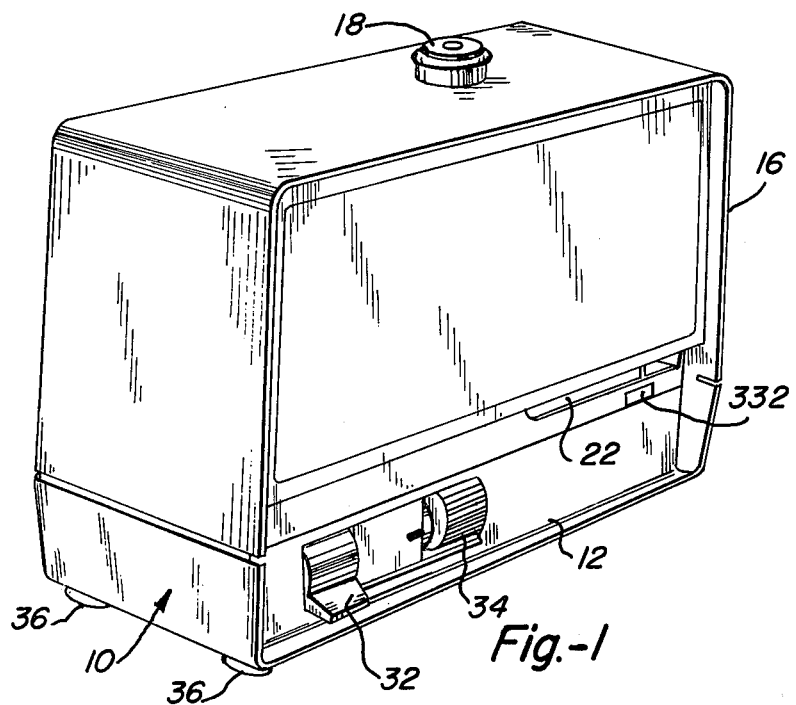
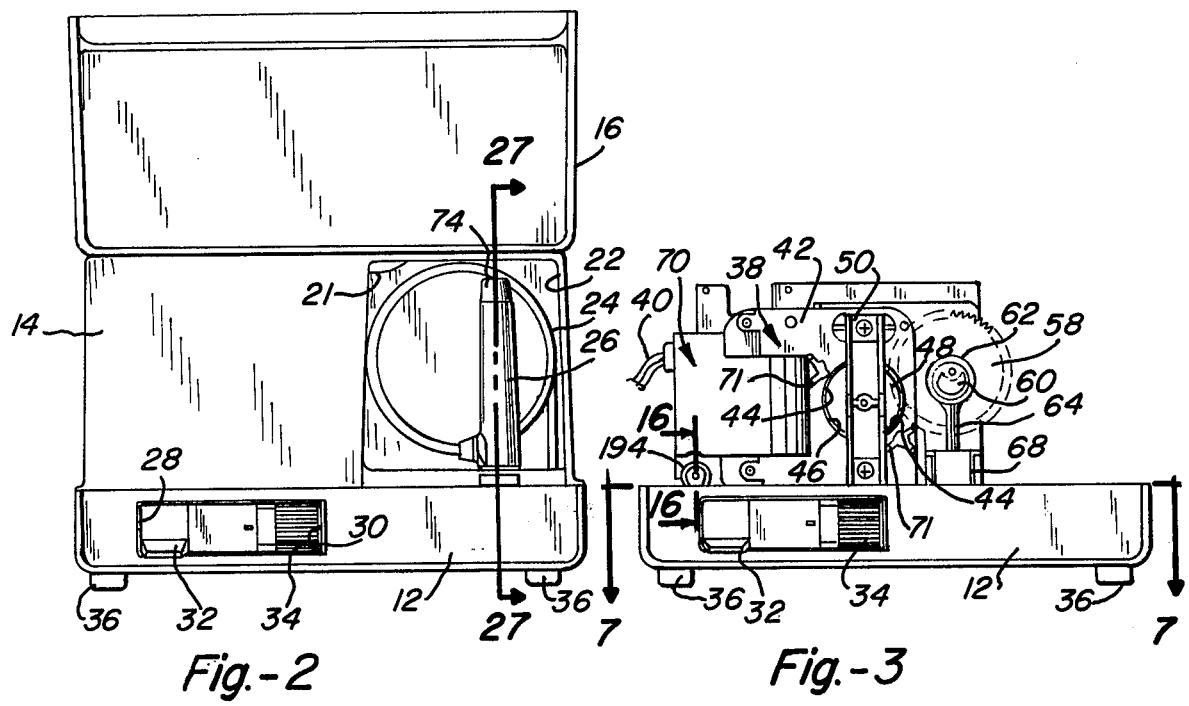
Fig.-1
Fig.-2    Fig.-3

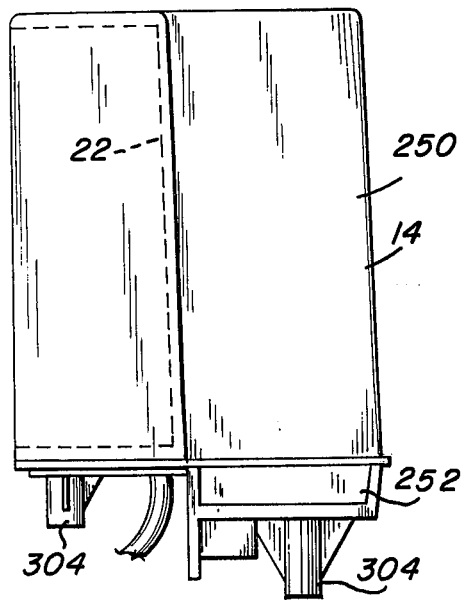
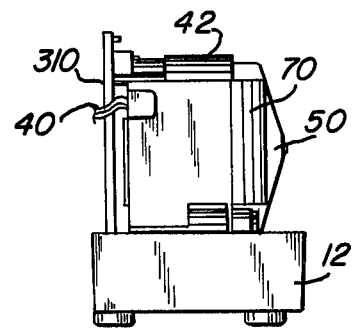
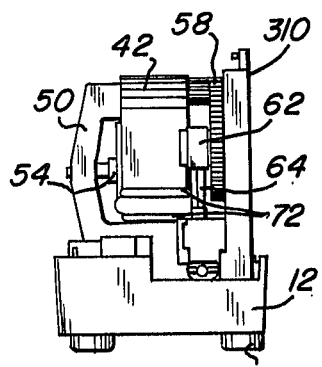
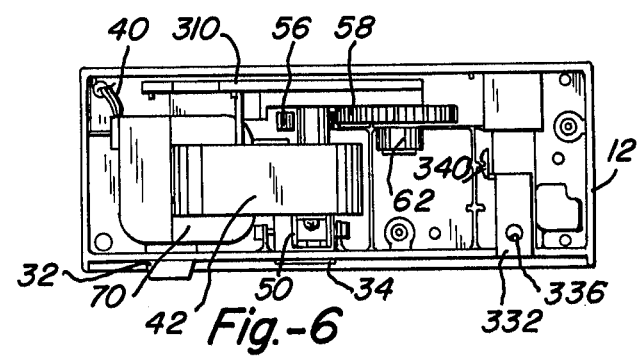
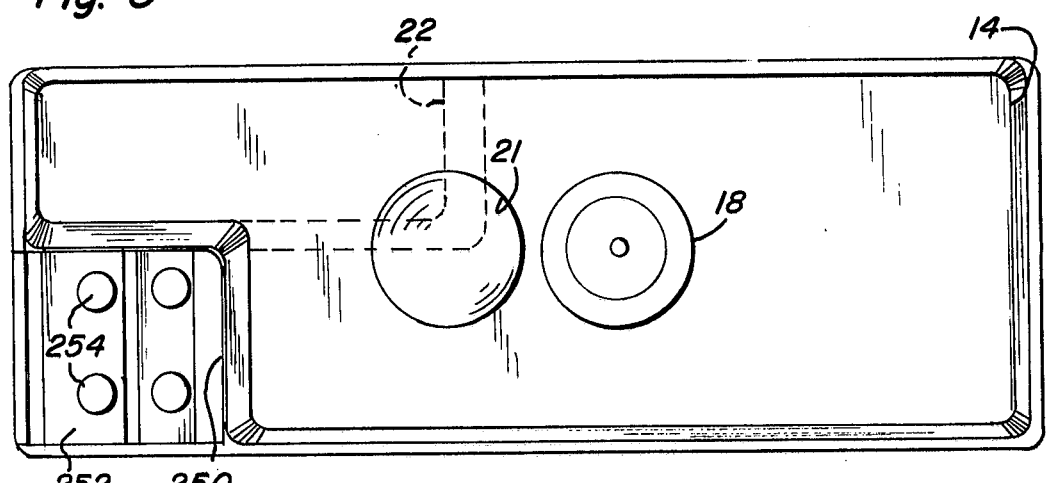

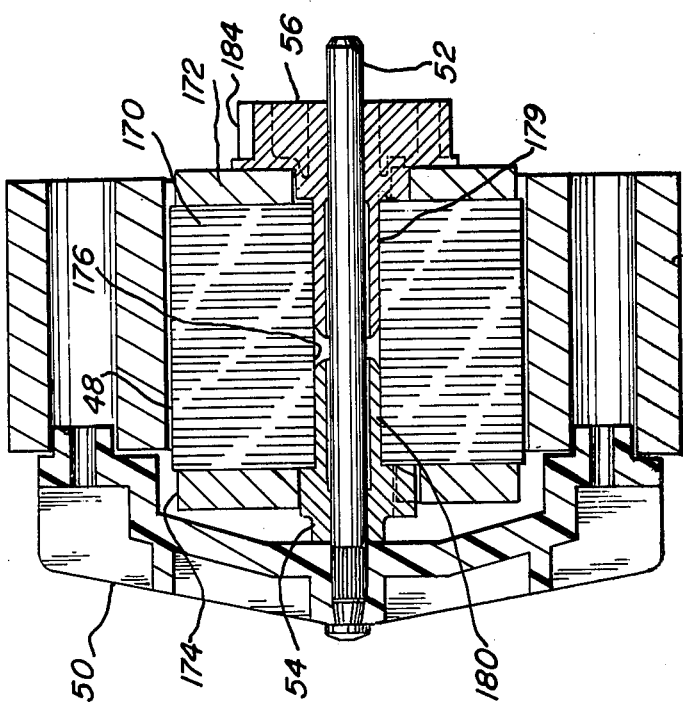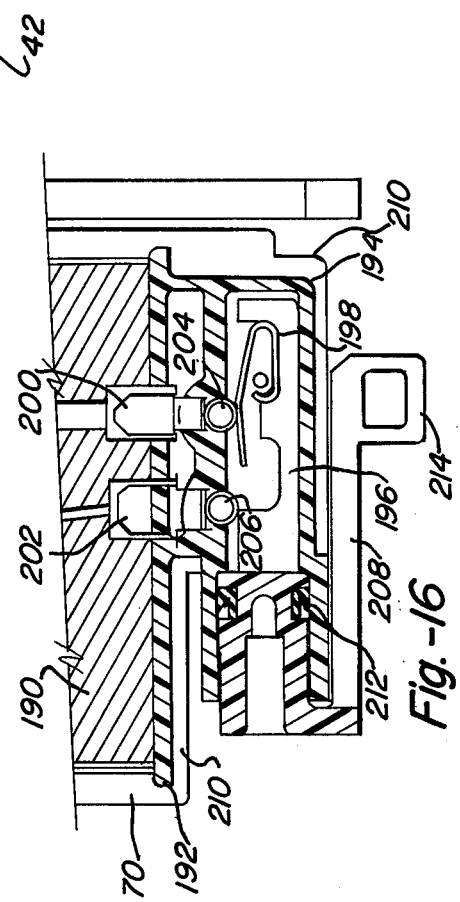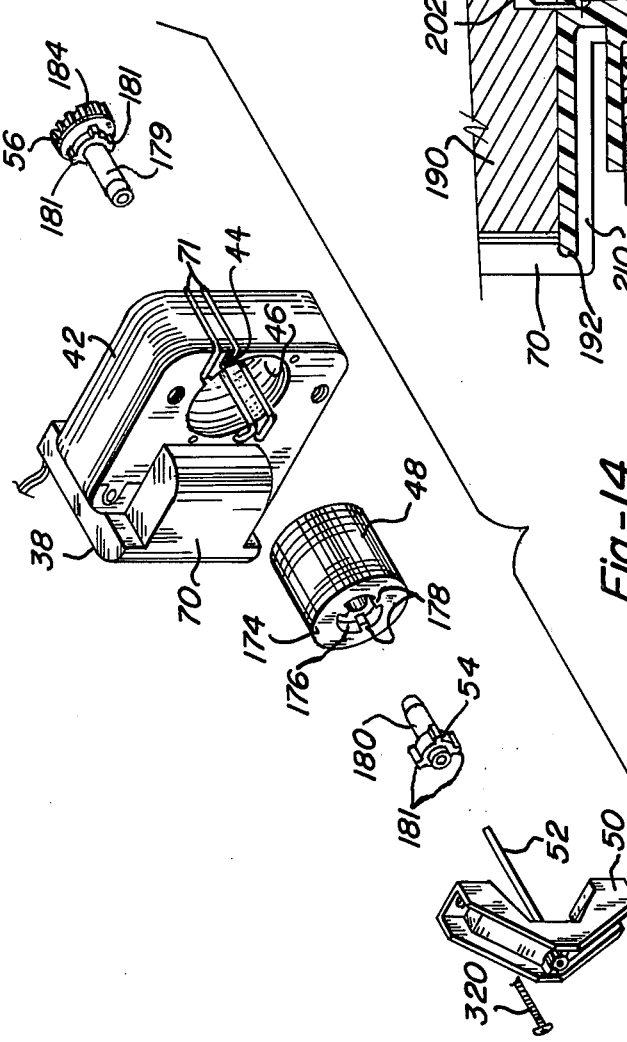

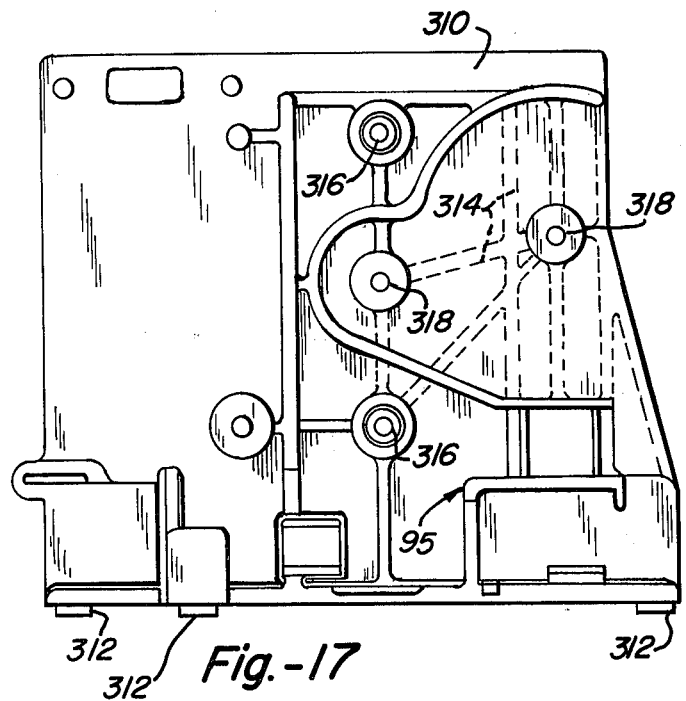
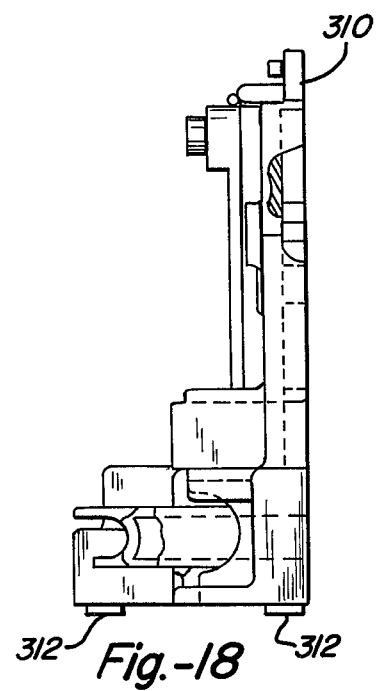
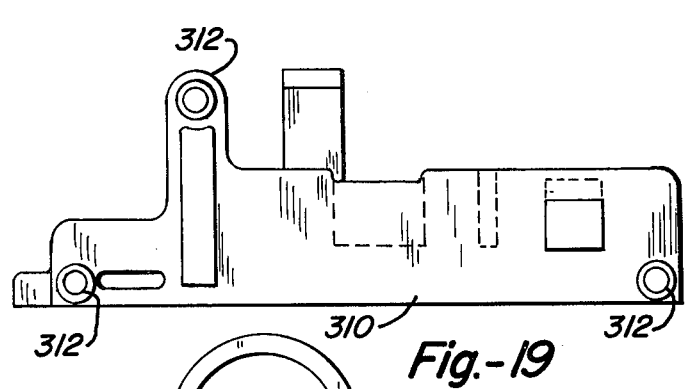
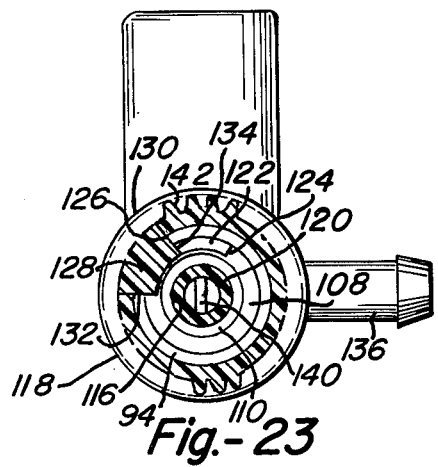
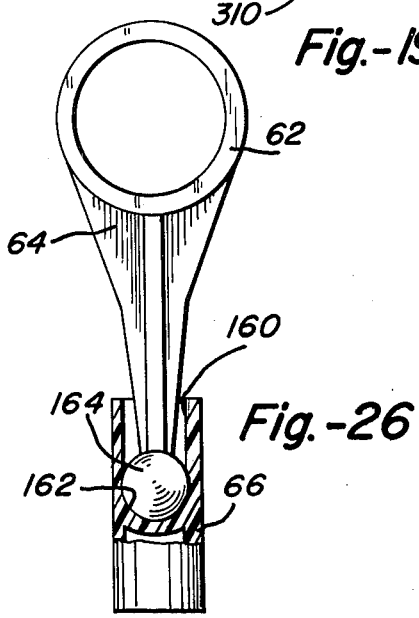

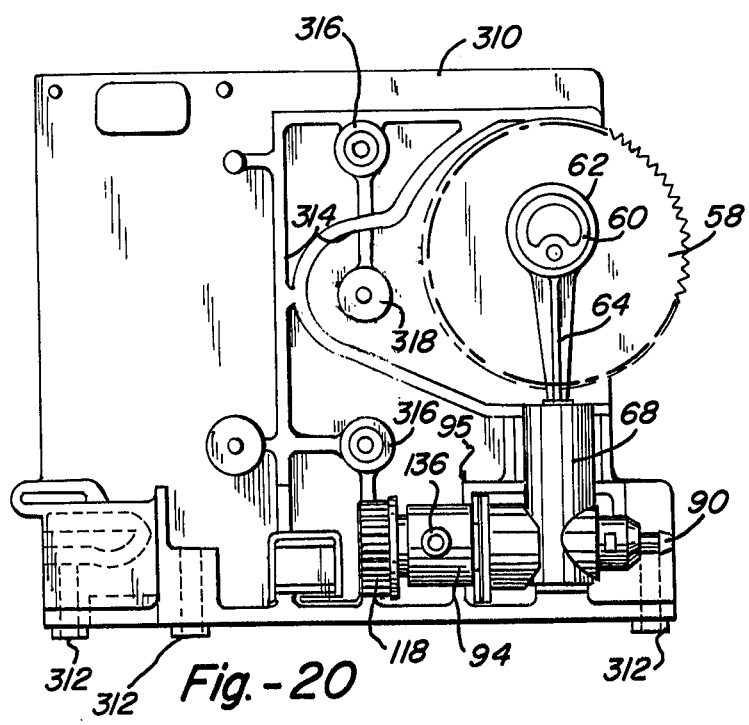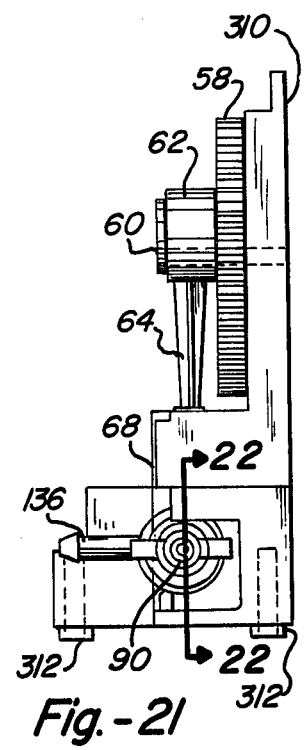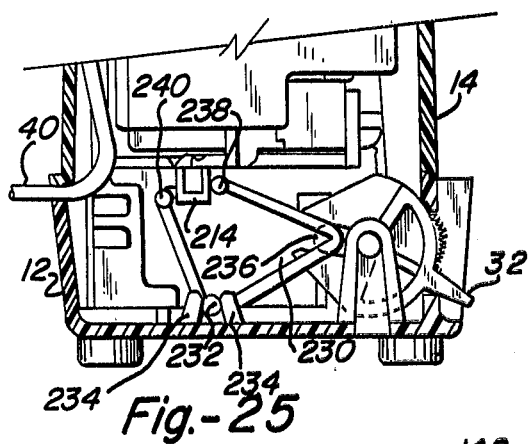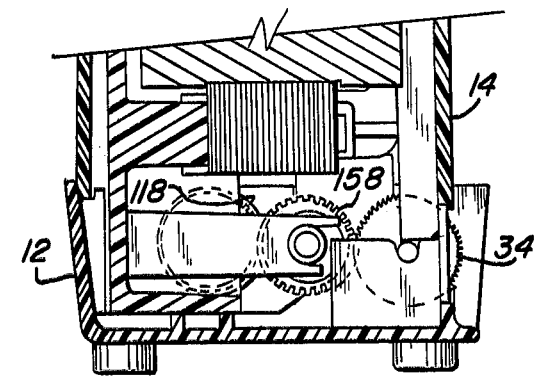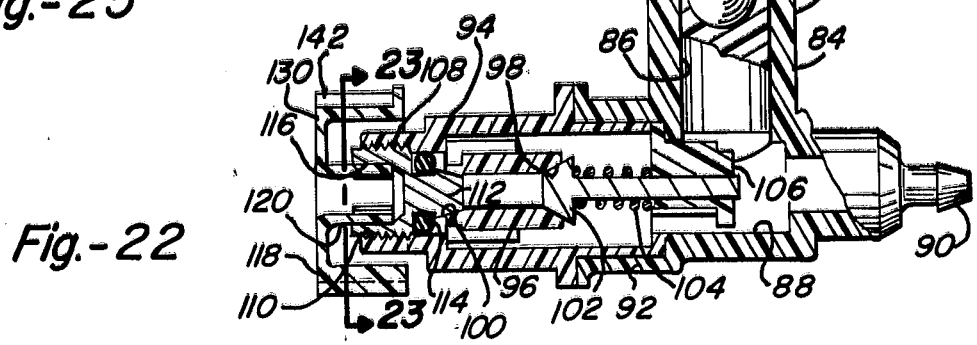

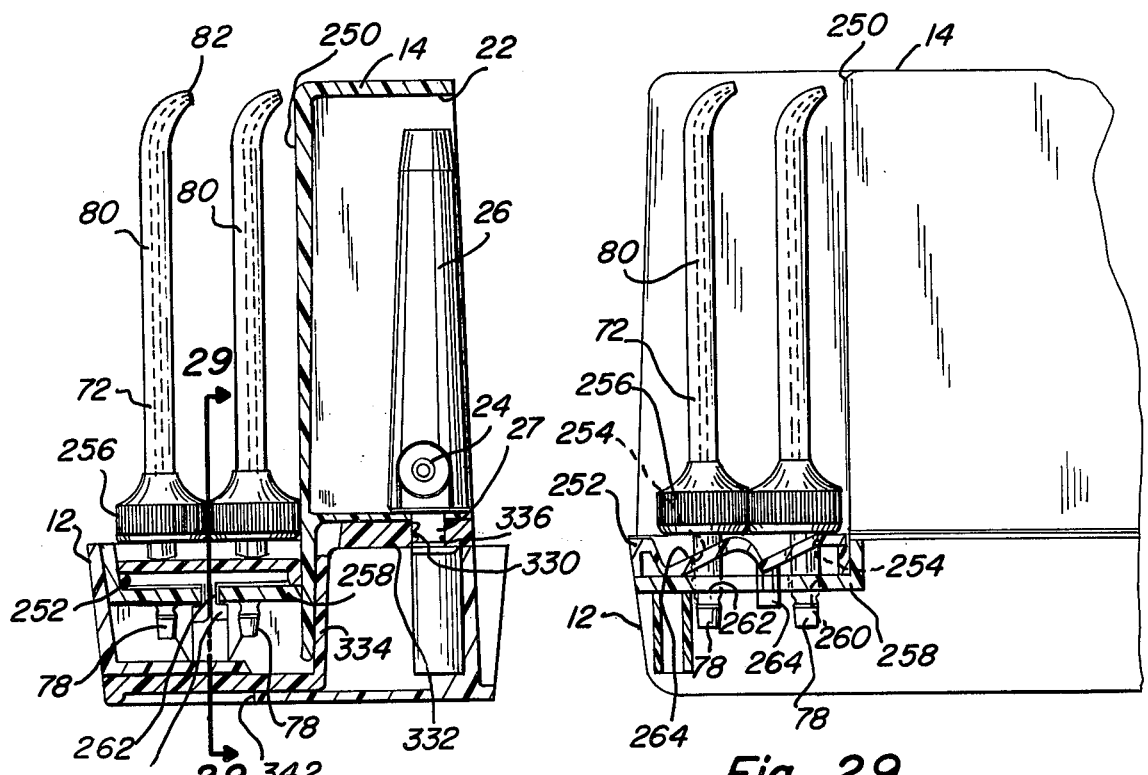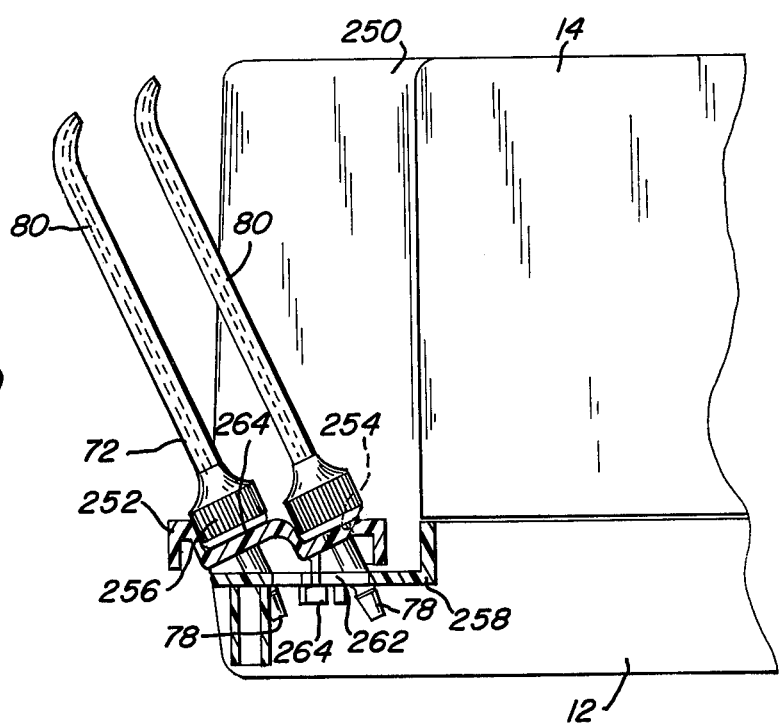

DENTAL SYRINGE

The present invention pertains to appliances. More particularly, it relates to appliance features such as a combined motor-switch combination, an improved piston-driving connection in a pump, a pressure control for use with such a pump and an arrangement for mounting the rotor of the motor.

One kind of appliance which has been the subject of widespread consumer acceptance is an oral hygiene device for providing pulsed jets of water which are directed against the teeth and gums for the purpose of cleaning the teeth and massaging the gums. Methods and apparatus for this purpose are described and claimed in U.S. Pat. Nos. 3,227,158, Re. 27,274, 3,453,969, 3,467,083 and 3,425,410. All of those patents are assigned to the same assignee as the present application. The commercial appliances which have included the inventions of those patents having usually involved an attractively styled unit having a removable cover which, when inverted, serves as a reservoir for water supplied to the unit. Within the unit is a motordriven pump the outlet of which is coupled through a flexible hose to a hand-held jet tip or nozzle that the user employs to direct the pulsating jets against his teeth and gums. Typically included is a bypass type of liquid pressure control, an on-off switch and some facility for storing the hose and one or more nozzles when not in use. Desirably, such storage is beneath the cover that also serves as a reservoir.

In an effort to achieve durability in operation while at the same time effecting a maximum of manufacturing economy, attention has been given to the formation of as many components as possible from plastic material. Even the pump cylinder block and the cooperating piston have successfully been molded and formed from plastic.

While all this began in connection with oral hygiene devices such as those described in the aforementioned patents, the same apparatus also has found usage in other implementations such as wound debridement, cleaning of openings such as the ear canal and other medical applications. In addition, at least some of the mechanical improvements have been of a nature to lend themselves to employment in entirely different environments. What follows is a description of specific embodiments of improved oral hygiene appliances. At the same time, it will be recognized that the detailed features of improvement have application to other than appliances useful strictly in the oral hygiene field. Accordingly, it is a general object of the present invention to provide new and improved features useful in oral hygiene appliances and also having beneficial application elsewhere.

Another object of the present invention is to provide a new and improved switch assembly incorporated in connection with the energizing winding of an electric motor.

A further object of the present invention is to provide a new and improved coupling between a piston rod and a driven piston.

Still another object of the present invention is to provide a new and improved arrangement for adjusting pressure in a liquid supply system.

A still further object of the present invention is to provide a new and improved method of mounting a rotor within the stator of a motor.

An overall object, therefore, is specifically to improve oral hygiene appliances while at the same time devising features of improvement not only useful therein but also finding beneficial employment in a wide variety of implementations.

One aspect of the invention involves a device that includes a supply of liquid, a pump for propelling the liquid, means for delivering the propelled liquid to a point of use and a control for adjusting the pressure of the delivered liquid. The control includes a passage through which the liquid is propelled by action of the pump, a bypass for the passage and a valve for adjustably throttling the amount of the liquid conducted in the bypass. That valve has a rotatable stem carried within a sleeve having means defining a pair of stops circumferentially displaced around the axis of the sleeve, and the stem has a cylindrical surface concentric with the axis. A control knob has a pair of radial abutments respectively cooperative with the stops to limit rotation of the knob around the axis between corresponding positions of high and low pressure of the propelled liquid outletting the pump. The knob also includes a tube engageable concentrically with the cylindrical surface and fixedly secured thereto during assembly when one of the stops is engaged with one of the abutments while the stem is at one limit of rotation.

In another aspect of the invention, a device includes a supply of liquid, a pump for propelling the liquid and means for delivering the propelled liquid to a point of use. The pump includes a cylinder, a piston reciprocating within the cylinder and a piston rod that drives the piston in reciprocation. One end portion of the piston defines an outwardly opening internal recess the walls of which internally define a resilient spherical seat. A spherical bearing formed on one end of the piston is matingly received within the spherical seat.

In accordance with a further aspect, there is included an electric motor assembly which has a rotor, a structure for concentrating a magnetic field delivering energy to the rotor, a switch for supplying electrical power to the motor, an electrical winding on the structure that has electrical terminals and is responsive to the electrical power for inducing the magnetic field, and a contact element included in the switch for selectively conductively bridging the terminals. An insulated carrier of the contact element enables movement of that element into the bridging connection. An insulated housing is receptive of the carrier and is fixedly related to the winding. An hermetic seal is effected entirely of the winding and the housing. Included are means for moving the carrier to effect movement of the element.

The features of the present invention which are believed to be novel are set forth with particularity in the appended claims. The organization and manner of operation of the invention, together with further objects and advantages thereof, may best be understood by reference to the following description taken in connection with the accompanying drawings, in the several figures of which like reference numerals identify like elements, and in which:

FIG. 1 is a perspective view of an oral hygiene appliance having its parts arranged in a storage condition;

FIG. 2 is a front-elevational view of the appliance of FIG. 1 but with a cover inverted so as to serve as a reservoir of liquid;

FIG. 3 is also a front-elevational view of the appliance of FIG. 1 but with the cover and an enclosing housing removed;

FIG. 4 is a left-end elevational view of FIG. 3;

FIG. 5 is a right-end elevational view of FIG. 3;

FIG. 6 is a top plan view of FIG. 3;

FIG. 13 is a right-end elevational view of the housing shown in FIG. 12;

FIG. 13a is a top plan view of the housing shown in FIGS. 11-13;

FIG. 14 is an exploded perspective view of a motor assembly incorporated into the apparatus as shown particularly in FIGS. 3, 5 and 6;

FIG. 15 is a cross-sectional view taken along the axis of the motor assembly of FIG. 14 as assembled;

FIG. 16 is an enlarged and fragmentary cross-sectional view taken along line 16—16 in FIG. 3;

FIG. 17 is a front-elevational view of a component mounting structure included within the device of FIG. 1 and as particularly shown in FIG. 6;

FIG. 18 is a right-end elevational view of FIG. 17;

FIG. 19 is a bottom plan view of FIG. 17;

FIG. 20 is a front-elevational view similar to FIG. 17 but with certain of the operating components mounted in place;

FIG. 21 is a right-end elevational view of FIG. 20;

FIG. 22 is an enlarged, fragmentary cross-sectional view taken along the line 22—22 in FIG. 21;

FIG. 23 is a fragmentary cross-sectional view taken along the line 23—23 in FIG. 22;

FIG. 24 is a fragmentary cross-sectional view taken as if along the line 9—9 in FIG. 7 but showing a modified version;

FIG. 25 is a fragmentary cross-sectional view taken as if along the line 8—8 in FIG. 7 but showing a modification;

FIG. 26 is an enlarged cross-sectional view of a piston assembly included in the apparatus as already indicated in others of the figures;

FIG. 27 is a fragmentary cross-sectional view taken along the line 27—27 in FIG. 2;

FIG. 29 is a fragmentary cross-sectional view taken along the line 29—29 in FIG. 27; and FIG. 30 is a view similar to FIG. 29 but with certain of the parts in a different position.

Figure 7:
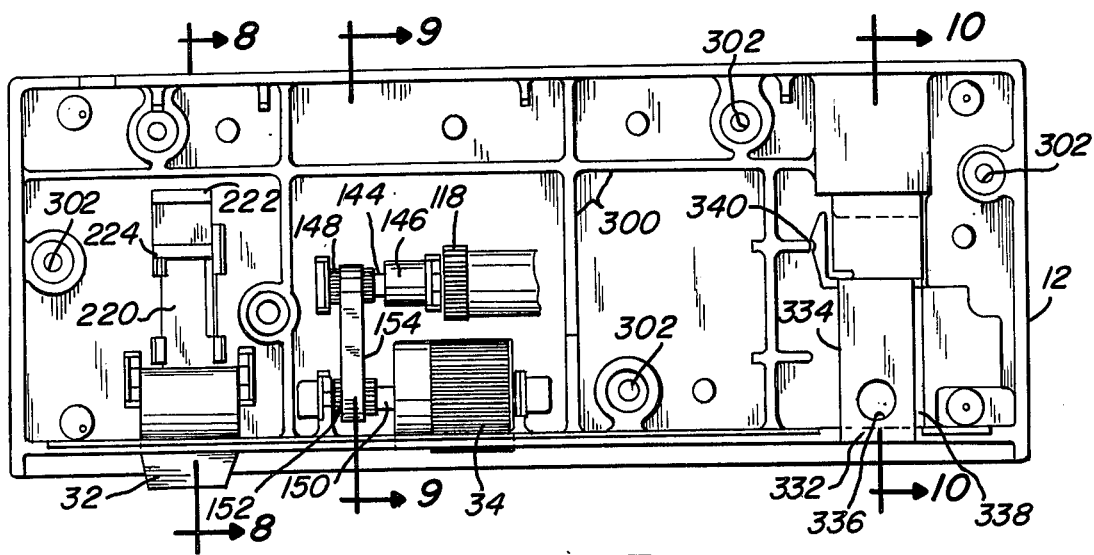
FIG. 7 is an enlarged fragmentary cross-sectional view taken along the line 7—7 in FIG. 3.

As particularly embodied, the appliance or device is in the form of oral irrigating apparatus for cleansing the teeth and massaging the gums. An enclosure 10 includes a base unit 12 from which upwardly projects a housing 14. Around its lower margin, housing 14 is slightly inset from the upper margin of base 12 so as to receive the walls of a cover 16 in an approach such that, with cover 16 in place, a generally smooth-walled exterior appearance of the entire appliance results.

Figure 11:
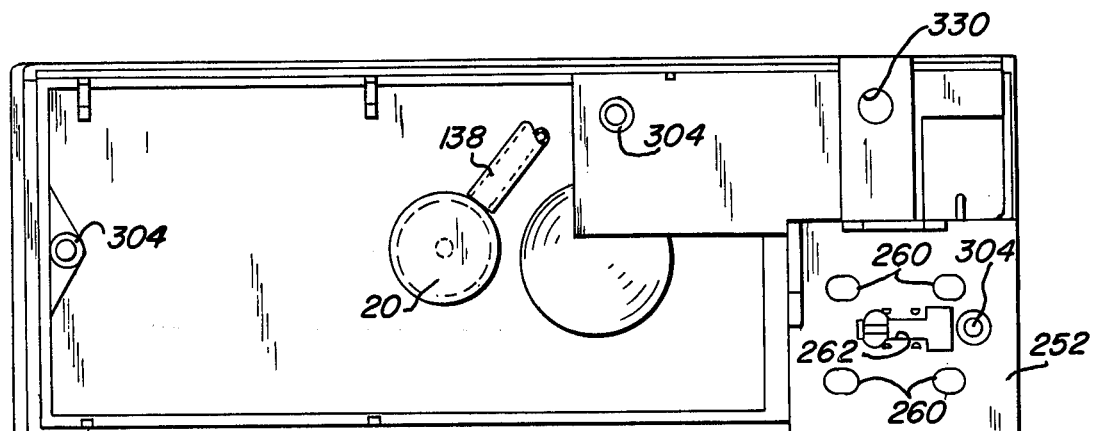
FIG. 11 is a bottom view taken along the line 11—11 in FIG. 12.
Figure 12:
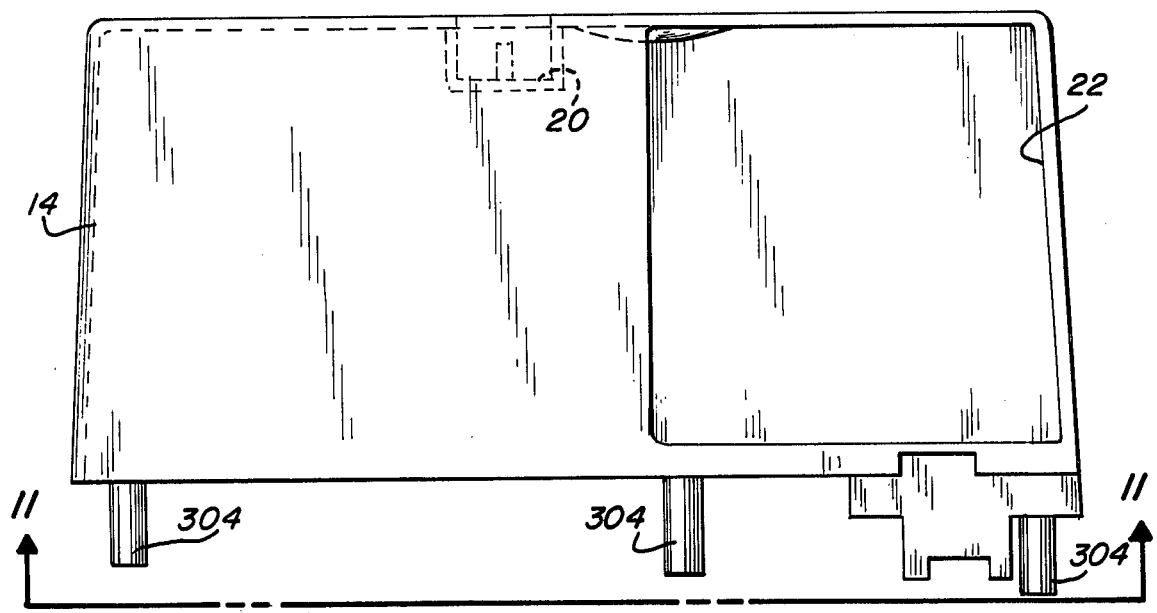
FIG. 12 is an enlarged front elevational view of the housing shown in FIG. 2 but removed in FIGS. 3-6.

Centrally located in the top wall of cover 16 in its orientation as shown in FIG. 1 is a valve 18 matable with an inlet coupling 20 (FIG. 11) when cover 16 is inverted and disposed atop housing 14 in the manner illustrated in FIG. 2. A depression 21 in the top wall of housing 14 accommodates the underside of valve 18 when cover 16 is in place as shown in FIG. 1. In the FIG. 2 position, cover 16 serves as a reservoir of water or other cleansing agent. Valve 18 preferably is of a gravity operated type so as to permit the downward flow of water from the reservoir into coupling 20 when the cover is in the FIG. 2 position.

Recessed into the front wall of housing 14 is a cavity 22 of sufficient size to accommodate a coiled flexible hose 24 connected at its outer end into a handle 26 the lower end of which as shown in FIG. 27 has a nub 27 which is seated within an opening provided in the bottom wall of cavity 22. With hose 24 and handle 26 so situated within cavity 22, they are at least substantially concealed when cover 16 is in its FIG. 1 position.

Base 12 of enclosure 10 has a front wall which includes a pair of openings 28 and 30. Projecting outwardly through opening 28 is a switch level 32, while a sector of a knurled wheel 34 projects outwardly through opening 30. Projecting downwardly from near each of the corners of base 12 are resilient feet 36. Switch level 32 serves to energize and de-energize the unit, while wheel 34 is a fluid pressure control.

Within the interior of housing 14 is an electric motor 38 energized from a power cord 40 through action of switch lever 32, one electrical lead within cord 40 effectively being connected or disconnected by action of the switch. Motor 38 includes a laminated-iron stator structure 42 of a modified C-shape so as to define air gaps 44 separating a pair of semicylindrical segments which together define a bore 46 within which is received a rotor 48 of mating cylindrical shape but of slightly smaller diameter. Rotor 48 is secured in place for rotation by a bracket 50 from which a spindle 52 projects axially through bore 46 and rotor 48 and on which rotor 48 is mounted by means of a bearing 54. On the opposite side of stator structure 42 from bracket 50 is a pinion gear 56 mounted coaxially to rotor 48 and meshing with a driven gear 58. Molded at one side axially of gear 58 is an eccentric bearing 60 encircled by a sleeve bearing 62 formed on one end of a connecting rod or piston rod 64 which reciprocates a piston 66 within the cylindrical piston bore of a pump 68. Encircling stator structure 42 opposite bore 46 is a winding assembly 70 which, in itself, serves to respond to the supplied electrical power to induce magnetic energy within stator 42 and through rotor 48. As indicated, motor 38 is of the shaded-pole variety, having shorted turns 71 disposed around air gaps 44 and functioning in a conventional manner.

In use, a jet tip 72 (FIG. 27) is plugged into the outer end 74 of handle 26 by means of a detachable coupling 78. Jet tip 72 includes an elongated sleeve 80 formed integrally with coupling 78 and bent laterally at its opposite end so that an outlet orifice 82 is capable of projecting fluid generally laterally to the axis of sleeve 80.

In operation, water from the reservoir formed by inverted cover 16 is drawn therefrom by pump 68 through valve 18 and delivered by way of hose 24 to orifice 82 of nozzle or jet tip 72. The water emerges from orifice 82 in a series of pulses or slugs. The ultimately produced water pressure, flow rate, pulse rate and orifice diameter are all within the ranges taught by the aforementioned U.S. Pat. No. 3,227,158. The overall mechanical functions of each of the different principal components are the same as those described with respect to the oral hygiene apparatus of the aforementioned U.S. Pat. No. Re. 27,274. Accordingly, the teachings of those two patents are incorporated herein by reference. Moreover, the operation of valve 18 and its cooperation with coupling or fitting 20 is the same as described in that reissue patent.

Turning now in more detail to the improvements, FIGS. 21-23 and 26 are pertinent to details of the pump and pressure control assemblies. Pump 68 has a pump body 84 in which is defined a cylindrical bore 86 and in which piston 66 is slidingly received. The lower end of piston 66 is internally recessed in a manner to form a skirt that engages the walls of bore 86 sealingly. The lower end of bore 86 opens into a chamber 88 from which exits a fitting 90 onto which the inner end of hose 24 is connected. Opposite fitting 90, chamber 88 opens laterally into a flanged extension 92 of chamber 88. A matingly flanged sleeve 94 is seated against and within extension 92 and when the unit is assembled is secured in place by an internal sub-housing 95 as best shown in FIG. 17. Concentrically secured within sleeve 94 is a cylinder 96 having respective valve seats 98 and 100 formed in its opposing ends. A valve 102 is urged against seat 98 by a spring 104 compressed between valve 102 and the oppositely facing surface of a valve guide 106 secured in place at the inner end of sleeve 94 and within the opening between chamber 88 and extension 92. Guide 106 is formed to permit fluid communication between chamber 88 and the additional chamber area defined within extension 92.

A necked-down portion 108 of sleeve 94 projects outwardly and away from pump body 84. Threadably received for rotation within portion 108 is the stem 110 of a valve 112 which cooperates with seat 100. Stem 110 and valve 112 are sealed within portion 108 by means of a resilient O-ring 114. The outer end of stem 110 is counterbored to define a cylindrical surface 116. A control knob 118 includes a centrally projecting tube 120 engageable concentrically within surface 116.

An ear 122 (FIG. 23) projects outwardly from the end of portion 108 of sleeve 94 so as to define a pair of spaced-opposed stops or surfaces 124 and 126. A lug 128 projects inwardly from a circumferential lateral wall 130 of knob 118 and thereby defines a pair of space-opposed surfaces that constitute radial abutments 132 and 134 which cooperate with stops 124 and 126 to limit rotation of knob 118 around the longitudinal axis of the assembly and between corresponding positions that, as will be seen, result in the control as between high and low pressure of the propelled liquid which outlets the pump. An inlet fitting 136 is ported at its internal end into the interior of cylinder 96. The external end of fitting 136 is coupled by a tube 138 to coupling or fitting 20 in the top wall of housing 14.

In operation, valve 102 serves as a check valve in a flow passage which extends from the interior of cylinder 96 through valve seat 98, the interior of extension 92 and chamber 88 to fitting 90. On the suction or upward stroke of piston 66, liquid is thus drawn from the reservoir and through the passage into chamber 88. On the reverse or pressure stroke of piston 66, the water is prevented by valve 102 from flowing rearwardly and thus is forced to exit through fitting 90 and into hose 24. The space between the internal wall of sleeve 94 and the external wall of cylinder 96 communicates from chamber 88 and the interior of extension 92 to the opening defined by valve seat 100. When valve 112 is closed against seat 100, all pressure developed by the downward stroke of piston 66 serves to propel the liquid through fitting 90. When valve 112 is at least partially open, however, a portion of the pressure developed by the downward stroke of piston 66 is expended in bypassing a part of the water back through seat 100 and into the reservoir through hose 138, overcoming the gravity operation of valve 18. Thus, valve 112 serves to throttle the amount of the liquid reversely conducted in the bypass.

During assembly of the pressure control system, stem 110 is first threaded within portion 108 until valve 112 is pressed against seat 100. Facilitating that operation is a screw-driver slot 140 formed in the bottom of the counterbore which defines surface 116. Knob 118 is then slipped into place by insertion of tube 120 within the counterbore. Immediately prior to that insertion, a drop of cement is applied over surface 116. Alternatively, cement may be applied through the inner end of tube 120. Upon such insertion, knob 118 is turned or rotated clockwise until abutment 134 engages stop 126. Thereafter, knob 118 is left undisturbed until the cement has cured. It will be observed that this operation results in fixing the rotative position of knob 118 with respect to the high pressure limit of operation in which the bypass is entirely closed by valve 112. Correspondingly, the circumferential extent of ear 122 and lug 128 are selected so as to limit the amount of opening of valve 112 to that which is desired for the limit of low pressure operation. Rotation of knob 118 to bring abutment 132 against stop 124 defines that limit. This approach avoids any necessity of calibrating the knob position with respect to pressure limits after assembly.

Figure 28:
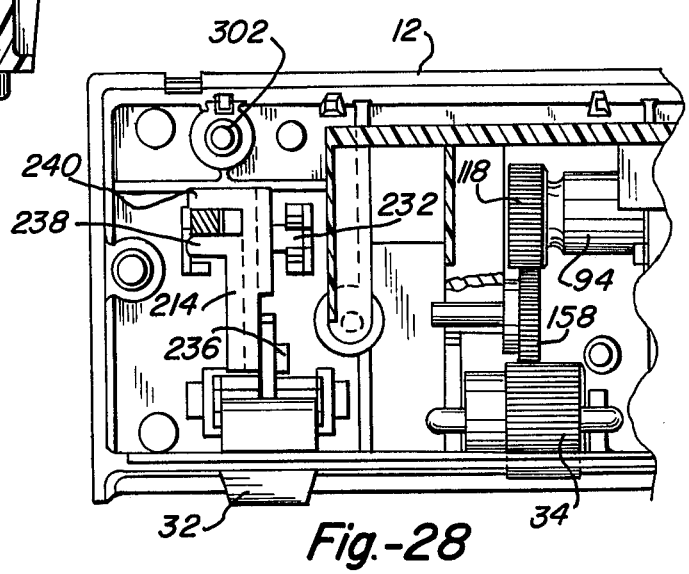
FIG. 28 is a fragmentary cross-sectional view taken as in FIG. 7 but showing the modification of FIGS. 24 and 25.

As shown, external or lateral wall 130 of knob 118 is formed to present a succession of gear teeth 142. If desired, the combined pump and pressure control assembly may be so located within enclosure 10 as to permit knob 118 to serve directly as knurled wheel 34. For the purpose of achieving compactness in the overall assembly, and particularly in minimizing or slimming the depth of the overall appliance, it is preferred to indirectly couple wheel 34 to knob 118. One embodiment to that end is detailed in FIGS. 7 and 9. In this version, a shaft 144 mounted from base 12 for rotation is joined axially at one end by a connector 146 to knob 118 and at its other end carries a spur gear 148. Similarly, a shaft 150, on which wheel 34 is rotatably carried from base 12, carries an axially displaced spur gear 152 oriented laterally with respect to gear 148. An endless belt 154, of resilient material such as rubber, serves to couple gears 148 and 152 for the transmission of motion therebetween. Desirably, belt 154 includes inwardly projecting lugs 156 cooperative with the teeth of gears 148 and 152. Alternatively as detailed in FIGS. 24 and 28, wheel 34 and knob 118 are coupled by means of a gear train established by the interpositioning therebetween of an idler gear 158, gear 158 being mounted for rotation from a mounting plate (310) to be described below.

As already indicated, pump body 68 and the components mechanically connected therewith are formed of plastic. The same is true of connecting rod 64. Moreover, and as detailed in FIG. 26, the upper end of piston 66 is shaped to define an outwardly opening internal recess 160 the walls of which internally define a resilient spherical seat 162. On the lower end of connecting rod 64 is formed a spherical bearing 164 that is matingly received within seat 162. This arrangement achieves a wrist-pin type of connection while yet allowing lateral freedom of alignment in all circumferential directions and, thus, reducing tolerance requirements as, for example, between the orientation of driven gear 58 and cylinder bore 86. At the same time, assembly of piston 66 to rod 64 involves only a simple snap fitting.

Directing attention now primarily to FIGS. 14 and 15, it will be observed that rotor 48 is composed of a stack of circular laminations or plates 170 sandwiched between circular end plates 172 and 174. Internal bores 176 within laminations 170 and plates 172, 174 accommodate receipt of the shafts on bearing 54 and pinion 56. Moreover, at least the portion of bore 176 defined by plates 172 and 174 includes circumferentially spaced longitudinally extending lugs 178 that project radially inward of the bore. Both a stepped shaft 179 projecting inwardly from pinion 56 and a stepped shaft 180 projecting inwardly from bearing 54 include circumferentially-spaced longitudinal ribs 181 that project radially outward thereof. Lugs 178 and ribs 181 interfit circumferentially and are of such radial extent as to enable a secure press fit of shafts 179 and 180 securely within bore 176. Of course, each of shafts 179 and 180 extend only partly into bore 176 in order to allow tolerance. For transmitting motive power to driven gear 58, pinion 56 is externally formed to include gear teeth 184.

As would be conventional, one wire in power core 40 might be routed through an electrical switch of which lever 32 would be a directly-connected and encased part. However, that leads to the need for additional wiring on beyond the switch back to motor 38 and may encounter certain additional obstacles imposed by regulations pertaining to double-insulation requirements and the like. Accordingly, attention is next directed to the combined motor winding and switch contact arrangement detailed in FIG. 16. Winding assembly 70 includes a multi-turn coil 190 of wire wound upon a bobbin 192 of insulative material and which encircles the corresponding leg of stator structure 42. In itself, this mode of mounting an energizing coil upon the stator of a motor is well known. In this case, however, a switch housing 194 of insulative material is fixedly related to winding 190 and, in particular, is formed integrally with bobbin 192. Slidingly received for longitudinal movement within housing 194 is an insulated carrier 196 that supports an electrical contact element 198. Brought out through the lateral wall of bobbin 192 are a pair of electrical conductors 200 and 202 that constitute one lead extending from power cord 40 for the enablement of selective energization of motor 38. Respective terminals 204 and 206 project through the wall of housing 194 and are so oriented as to be electrically bridged by a leg of contact 198 when carrier 196 is moved to the left from the position shown in FIG. 16. Housing 194 is open at one longitudinal end from which carrier 196 projects and then is reentrantly turned or bent so as to have an operating member 208 disposed alongside the exterior of housing 194. Thus, movement of member or arm 208 enables selective bridging and unbridging of terminals 204 and 206 by element 198.

Both winding 190 and housing 194 are entirely hermetically sealed. To this end, bobbin 192, including coil 190, is entirely encapsulated by a seal material 210. In addition, the seal material is extended around the exterior of housing 194 except for its entrance that receives carrier 196. Completing the seal, a resilient lip seal 212 is disposed between carrier 196 and the inner wall of housing 194. Desirably, a protective thermal cut-off is wired in series with one of conductors 200 and 202 and disposed on bobbin 192 so as also to be encapsulated. Of course, the cut-off opens the energizing circuitry upon the occurrence of over heating of the motor.

If desired, arm 208 might be extended directly through an opening in a wall of enclosure 10 so as to serve as a switch operator. Preferably, however, arm 208 is coupled indirectly to switch lever 32. To that end, a tab 214 projects outwardly, and in this case downwardly as shown, from arm 208. One version of this coupling arrangement is detailed in FIG. 8. Thus, switch lever 32 includes a pinion 216 cooperative with a rack 218 formed on a rigid carriage 220 mounted in the bottom of base 12 so as to be slidable fore and aft. Upstanding from and formed as a part of carriage 220 are a pair of stubs 222 and 224 that embrace tab 214 so as to enable the transmission of movement to carrier 196.

An alternative form of coupling between switch lever 32 and tab 214 is illustrated in detail in FIG. 25. In this case, the coupling means includes a rocking arm 230. Arm 230 includes a first pivot pin 232 captivated by lugs 234 projecting upwardly from the bottom of base 12 so as to enable rocking of the arm. Another pin 236 projects laterally from the rear of the assembly of switch lever 32 and engages a corresponding seat formed in arm 230 so as to effect the rocking action of the arm in response to movement of lever 32. In addition, a pair of pins 238 and 240, projecting laterally from a third corner of arm 230, embrace opposite sides of tab 214 so as to establish a pivotal coupling which enables movement of carrier 196 in response to deflection of lever 32 and the consequent occurrence of rocking action of arm 230.

At the right-rear corner of housing 14 from the view of FIG. 2 is an inward recess 250 extending from the outer margin of base 12 along a rearward portion of the base (FIG. 27). Recess 250 thus defines a cavity which is concealingly enclosed by cover 16 when the latter is in the position as shown in FIG. 1. A shelf 252 is supported on base 12 for slidable movement between a first position concealed within cover 16 when the latter is in the position of FIG. 1 and a second position in which the shelf projects outwardly from base 12 when cover 16 is removed. Shelf 252 includes a plurality of oval shaped openings 254 that are receptive of the lower ends of jet tips or nozzles 72, specifically including fittings 78, for the purpose of holding the nozzles in an upright position. Shelf 252 is associated with means for effecting an outward tilt of the upper ends of jet tips 72 laterally away from base unit 12 when shelf 252 is moved to its outwardly extended second position as shown in FIG. 30. Knobs 256 on nozzles 72 serve to seat the nozzles on top of shelf 252.

In more detail, shelf 252 rides on top of a plate 258 formed as a part of housing 14 and underlying shelf 252. Spaced below each of openings 254 when shelf 252 is in its closed position is a corresponding oval-shaped opening 260 in plate 258 and also of a size to receive fitting 78. A keyway 262 is formed in plate 258 for receipt and captivation of a lug 264 that depends downward from shelf 252 and mounts the shelf for sliding movement upon the plate. It may be noted that keyway 262 is T-slotted at one end to permit removal of shelf 252 for the purpose of cleaning that shelf and plate 258.

Shelf 252 is corrugated in cross section so as to define inclined upper faces 264 toward which the bottom surfaces of knobs 256 are disposed. When shelf 252 is in its closed position as shown in FIG. 29, nozzles 72 are held in a vertical position by the alignment of respective openings 254 and 260. On the other hand, movement of shelf 252 to its open position as shown in FIG. 30 causes nozzles 72 to be tilted outwardly from the unit so as to be more accessible to the user.

Base unit 12 is interlaced on its interior with a plurality of strength-giving reinforcing ribs as indicated at 300 as an example. In addition, upwardly projecting hollow bosses such as at 302 serve to enable the affixation to mating posts 304 downwardly depending from the bottom of housing 14. Other lugs, ears or the like projecting upward from the bottom of base 12 serve to mount the different mechanical components already described. As shown, the different bosses are secured to their respective posts by means of screws inserted from the bottom of base 12.

Facilitating assembly of the entire unit into a compact package is the inclusion of an upright mounting plate 310 securable at its lower end by means of posts 312 to suitable ones of additional bosses 302 projecting upward from the bottom wall of base 12. Here again, plate 310 includes a plurality of reinforcing ribs 314. In addition, various bosses 316 and 318 project laterally outward from wall 310 in order to receive different securing elements or spindles. As shown in FIGS. 17 and 20, for example, driven gear 58 is mounted for rotation by a spindle which extends into the hollow bore of a corresponding boss 318. Similarly, spindle 52 is received within the opening in a boss 318 that is bridged by bosses 316 which receive screws 320 that serve to mount stator 42 of the motor and also position rotor 48 in place. Primarily, then, mounting plate 310 serves as a subassembly base for supporting such elements as motor 38 and its drive train associated with pump 68.

Figures 8, 9:
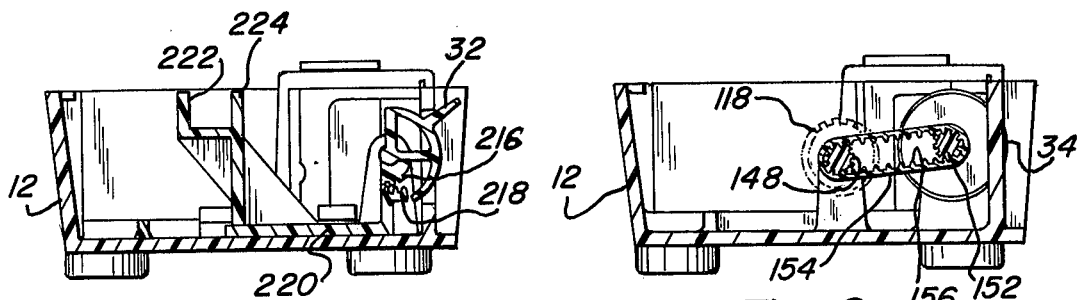
FIG. 8 is a cross-sectional view taken along the line 8—8 in FIG. 7.
FIG. 9 is a cross-sectional view taken along the line 9—9 in FIG. 7.
Figure 10:
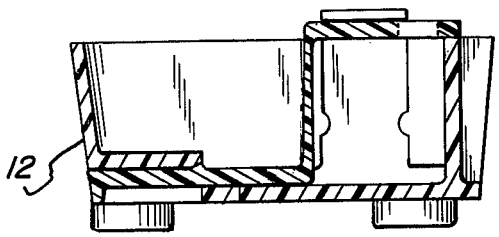
FIG. 10 is a cross-sectional view taken along the line 10—10 in FIG. 7.

Referring again to FIG. 27, nub 27 of handle 26 is received within an opening 330 in the bottom wall of cavity 22. Underlying that bottom wall is a portion 332 of a support 334 that has an opening 336 aligned beneath opening 330 when support 334 is in the position shown in FIG. 27. As shown in FIGS. 6, 7 and 27, support 334 is guided for movement by a projection 338 upstanding from base 12 and a detent 340 also associated with base 12. An opening 342 in the bottom wall of base 12 provides user access to support 334 for the purpose of pulling the support outwardly of the unit. In that position, handle 26 may be mounted on support 334 in front of the unit, as when a nozzle 72 is left connected to handle 26 and cover 16 remains in its reservoir condition.

It will thus be seen that appliances have been described which feature a constructional arrangement permitting compactness and slimness in overall design. In addition, they include such features as a pressure control arrangement that permits the application during assembly of the pressure-determining knob or cap in a manner obviating any need for subsequent adjustment. Within the pump itself is included a most simple but yet quite effective coupling between a piston and a connecting rod. The overall motor assembly includes an effectively encapsulated cooperating switch mechanism. Another advantageous feature involves a secure but very simply effected mounting for the rotor within such a motor. A further feature of advantageous employment is a tilt-out shelf for storage of nozzles when the latter are not in use, such storage being entirely concealable by a removable cover that also serves as a reservoir.

While particular embodiments of the invention have been shown and described, it will be obvious to those skilled in the art that changes and modifications may be made without departing from the invention in its broader aspects, and, therefore, the aim in the appended claims is to cover all such changes and modifications as fall within the true spirit and scope of the invention.

We claim:

1. In a hygienic device which includes a supply of liquid, a pump for propelling said liquid in pulses of flow, a motor having a rotor for driving said pump, a switch for supplying electrical power to said motor, means for delivering the propelled liquid to a point of use and a control for adjusting the pressure of the delivered liquid, the improved combination comprising:

a structure in said motor for concentrating a magnetic field delivering energy to said rotor;

an electrical winding on said structure having electrical terminals and responsive to said electrical power for inducing said magnetic field;

a contact element included in said switch and moveable for selectively conductively bridging said terminals;

an insulated carrier of said contact element for enabling movement of said element into and out of bridging connection;

an insulated housing receptive of said carrier and fixedly related to said winding;

means for effecting an hermetic sealing entirely of said winding and said housing;

means for moving said carrier to effect movement of said element;

said pump including a cylinder, a piston reciprocating within said cylinder and a piston rod for driving said piston in reciprocation;

one end portion of said piston defining an outwardly opening internal recess the walls of which internally define a resilient spherical seat;

a spherical bearing formed on one end of said piston rod and matingly received within said spherical seat;

said control including a passage through which said liquid is propelled by action of said pump, a bypass for said passage and a valve for adjustably throttling the amount of said liquid conducted in said bypass;

said valve including a rotatable stem carried within a sleeve having means defining a pair of stops circumferentially displaced around the axis of said sleeve and said stem having a cylindrical surface concentric with said axis;

a control knob having a pair of radial abutments respectively cooperative with said stops to limit rotation of said knob around said axis between corresponding positions of high and low pressure of the propelled liquid outletting said pump, said knob also including a tube engageable with said cylindrical surface and fixedly secured thereto during assembly when one of said stops is engaged with one of said abutments while said stem is at one limit of rotation;

said motor including a cylindrical rotor having a bore with circumferentially-spaced longitudinal lugs projecting radially inward thereof;

and a cylindrical bearing member having circumferentially-spaced longitudinal ribs projecting radially outward thereof, said lugs and ribs interfitting circumferentially and being of a radial extent enabling a secure press fit of said bearing member within said bore.

2. In a device which includes a supply of liquid, a pump for propelling said liquid, means for delivering the propelled liquid to a point of use and a control for adjusting the pressure of the delivered liquid, the improvement comprising:
  said control including a passage through which said liquid is propelled by action of said pump, a bypass for said passage and a valve for adjustably throttling the amount of said liquid conducted in said bypass;
  said valve including a rotatable stem carried within a sleeve having means defining a pair of stops circumferentially displaced around the axis of said sleeve, and said stem having a cylindrical surface concentric with said axis;
  a control knob having a pair of radial abutments respectively cooperative with said stops to limit rotation of said knob around said axis between corresponding positions of high and low pressure of the propelled liquid outletting said pump;
  said knob also including a tube engageable concentrically with said cylindrical surface and fixedly secured thereto during assembly when one of said stops is engaged with one of said abutments while said stem is at one limit of rotation.

3. A device as defined in claim 2 in which said cylindrical surface is fixedly secured to said tube while said stem is at a limit of rotation with said valve maintaining said bypass in a closed condition.

4. A device as defined in claim 2 in which said cylindrical surface is defined by the inner wall of a hollow portion of said stem projecting away from said valve, and in which said tube projects along the rotational axis of said knob and within said hollow portion of said stem.

5. A device as defined in claim 4 in which said stops are defined by space-opposed surfaces on an ear projecting away from the body of said sleeve, and in which said abutments are defined by space-opposed surfaces on a lug projecting inwardly from a circumferential lateral wall of said knob disposed concentrically with said axis.

6. A device as defined in claim 2 in which said knob includes a circumferential external wall, and in which a succession of gear teeth are formed around the exterior surface of said wall.

7. A device as defined in claim 2 which includes an enclosure within the interior of which said control is disposed and means within one wall of said enclosure defining an opening, a knurled wheel mounted within said enclosure for rotation and oriented to project a portion of its knurled surface through said opening, and coupling means transmitting rotational motion of said wheel into rotational motion of said knob.

8. A device as defined in claim 7 in which said coupling means includes an endless belt of resilient material coupled between said wheel and said knob.

9. A device as defined in claim 7 in which the knurling of said wheel is formed to constitute a succession of gear teeth, in which said knob includes a circumferential external wall formed to present a succession of gear teeth, and in which said wheel and said knob cooperate in a gear train that enables turning of said wheel to effect rotation of said stem.

10. In a device which includes a supply of liquid, a pump for propelling said liquid, and means for delivering the propelled liquid to a point of use, the improvement comprising:
  said pump including a cylinder, a piston reciprocating within said cylinder and a piston rod for driving said piston in reciprocation, said piston being entirely formed of plastic material;
  one end portion of said piston defining an outwardly opening internal recess the walls of which internally define a resilient spherical seat;
  and a spherical bearing formed on one end of said piston rod and matingly received within said spherical seat, both said piston rod and said bearing also being formed of plastic material.

11. In a device which includes a supply of liquid, a pump for propelling said liquid, and means including a user-held handle for delivering the propelled liquid to a point of use, the improvement comprising:
  a housing in which said pump is disposed;
  a recess formed in said housing to accept said handle in a storage position;
  and a support moveably mounted with respect to said housing and retractable away therefrom to mount said handle in a position outside said recess.

12. A device as defined in claim 11, in which said support includes means for mounting said handle within said recess when said support is in a storage position.

* * * * *